US007815045B2

(12) United States Patent
Delaney et al.

(10) Patent No.: US 7,815,045 B2
(45) Date of Patent: Oct. 19, 2010

(54) MID-STREAM FLUSHING ADAPTER ASSEMBLY

(75) Inventors: James P. Delaney, North Billerica, MA (US); K. Michael O'Rielly, Franklin, MA (US); Mark Girard, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 204 days.

(21) Appl. No.: 10/668,629

(22) Filed: Sep. 23, 2003

(65) Prior Publication Data

US 2005/0061698 A1 Mar. 24, 2005

(51) Int. Cl.
*A61M 25/00* (2006.01)
*B65D 85/00* (2006.01)

(52) U.S. Cl. .................. 206/364; 206/438; 206/571; 206/363

(58) Field of Classification Search ................ 206/363, 206/370, 438, 570–572, 364, 439, 461, 210; 604/334
See application file for complete search history.

(56) References Cited

U.S. PATENT DOCUMENTS

| 3,203,545 | A | * | 8/1965 | Grossman | 206/210 |
| 3,345,988 | A | | 10/1967 | Vitello | |
| 3,416,567 | A | * | 12/1968 | Tauberman et al. | 137/605 |
| 3,606,001 | A | * | 9/1971 | Talonn et al. | 206/364 |
| 3,861,395 | A | * | 1/1975 | Taniguchi | 604/172 |
| 4,805,611 | A | * | 2/1989 | Hodgkins | 128/207.14 |
| 4,925,448 | A | * | 5/1990 | Bazaral | 604/171 |
| 5,427,114 | A | * | 6/1995 | Colliver et al. | 600/561 |
| 6,053,313 | A | * | 4/2000 | Farrell et al. | 206/364 |
| 6,258,072 | B1 | * | 7/2001 | Weinberger | 604/284 |
| 6,375,006 | B1 | | 4/2002 | Samuels | |
| 6,569,106 | B1 | | 5/2003 | Ullman | |
| 6,588,588 | B2 | * | 7/2003 | Samuels | 206/364 |
| 2002/0144920 | A1 | | 10/2002 | Samuels | |

FOREIGN PATENT DOCUMENTS

WO    WO 93/03362 A    2/1993

* cited by examiner

*Primary Examiner*—Mickey Yu
*Assistant Examiner*—Steven A. Reynolds
(74) *Attorney, Agent, or Firm*—Fay Kaplun & Marcin, LLP

(57) ABSTRACT

Protective package for an elongated medical device, comprises a protective sheath including a lumen sized to receive a body of the elongated medical device, wherein a first end of the sheath is adapted to receive a distal end of the elongated medical device and a second end of the sheath is adapted to receive a proximal end of the elongated medical device and a hydration opening disposed between the first and second ends of the sheath. In addition, a method of packaging a medical catheter, comprises the steps of providing a substantially tubular enclosure having a lumen corresponding in inner diameter and length to dimensions of a catheter to be received therein and inserting a catheter into the lumen in combination with the steps of providing a hydration opening of the tubular enclosure in fluid communication with the lumen, the hydration opening directing a hydrating fluid in desired proportions toward proximal and distal ends of the catheter and providing a flushing adapter for connecting the hydration opening to a source of hydrating fluid.

25 Claims, 2 Drawing Sheets

MID-STREAM FLUSHING ADAPTER ASSEMBLY

BACKGROUND OF THE INVENTION

The use of catheters in medical procedures has become routine for the treatment of a multitude of ailments. Catheters have a variety of shapes and sizes, but generally include an elongated body that can be from several inches to several feet long, and a distal end which may be shaped as required to carry out the specific procedure for which the catheter is designed. The diameter of a catheter is typically much smaller than its length, such that the device has a generally cable-like appearance and structural properties. Catheters are often constructed with one or more lumens therein, which in general extend through most or all of the length of the catheter. These lumens may be employed to serve various functions at the catheter distal end including irrigation, providing suction, introducing medical instruments thereto, etc. The distal end may have a complex curvature, adapted to specific geometry of a target area in the body to facilitate reaching the target location or to facilitate carrying out the procedure.

When catheters are shipped, the packaging used is designed to carry out multiple functions. Since the catheter is hollow, the packaging has to protect the catheter from being crushed, and also from kinks which may be caused by bending the catheter's tubular body over too small a diameter. In particular, distal ends of catheters must be sufficiently protected from deformation, that the degree of care which must be exercised to ensure that the catheter arrives in condition for use is not excessive. The packaging often includes a tubular portion which contains the catheter's tubular body, while protecting it from bending and crushing. In many cases the tubular portion of the packaging is coiled to form a hoop, so that the elongated portion of the catheter may be packaged in a relatively small area. Coiling the protective hoop which contains the catheter simplifies the handling of the packaged catheter, since it is easier to process a package that is substantially round or square than it is to process a long, thin package shaped like a cable or tube.

Difficulties may also arise when removing the catheter from its protective package—particularly when the package is coiled in a hoop to make better use of the space available. Adhesion between the outer surface of the catheter and the inner surface of the protective tubular body may create a large amount of friction between the two surfaces, such that it is difficult to slide the catheter out of its protective packaging. In particular, when the catheter is not straight but has portions that are curved along specified shapes, separating the packaging from the device without damaging the catheter can be especially challenging. One solution is to hydrate the catheter, for example by injecting a water based solution or some other lubricant between the catheter and the packaging. However, this step may be complicated, since it is difficult to provide the fluid uniformly along the length of the entire catheter.

SUMMARY OF THE INVENTION

In one aspect, the present invention is directed to protective packaging for elongated medical devices comprising a protective sheath including a lumen sized to receive a body of the elongated medical device, wherein a first end of the sheath is adapted to receive a distal end of the elongated medical device and a second end of the sheath is adapted to receive a proximal end of the elongated medical device and a hydration opening disposed between the first and second ends of the sheath.

In addition, the present invention is directed to a method of packaging a medical catheter, comprising the steps of providing a substantially tubular enclosure having a lumen corresponding in inner diameter and length to dimensions of a catheter to be received therein and inserting a catheter into the lumen in combination with the steps of providing a hydration opening of the tubular enclosure in fluid communication with the lumen, the hydration opening directing a hydrating fluid in desired proportions toward proximal and distal ends of the catheter and providing a flushing adapter for connecting the hydration opening to a source of hydrating fluid.

DETAILED DESCRIPTION

Figure 1:
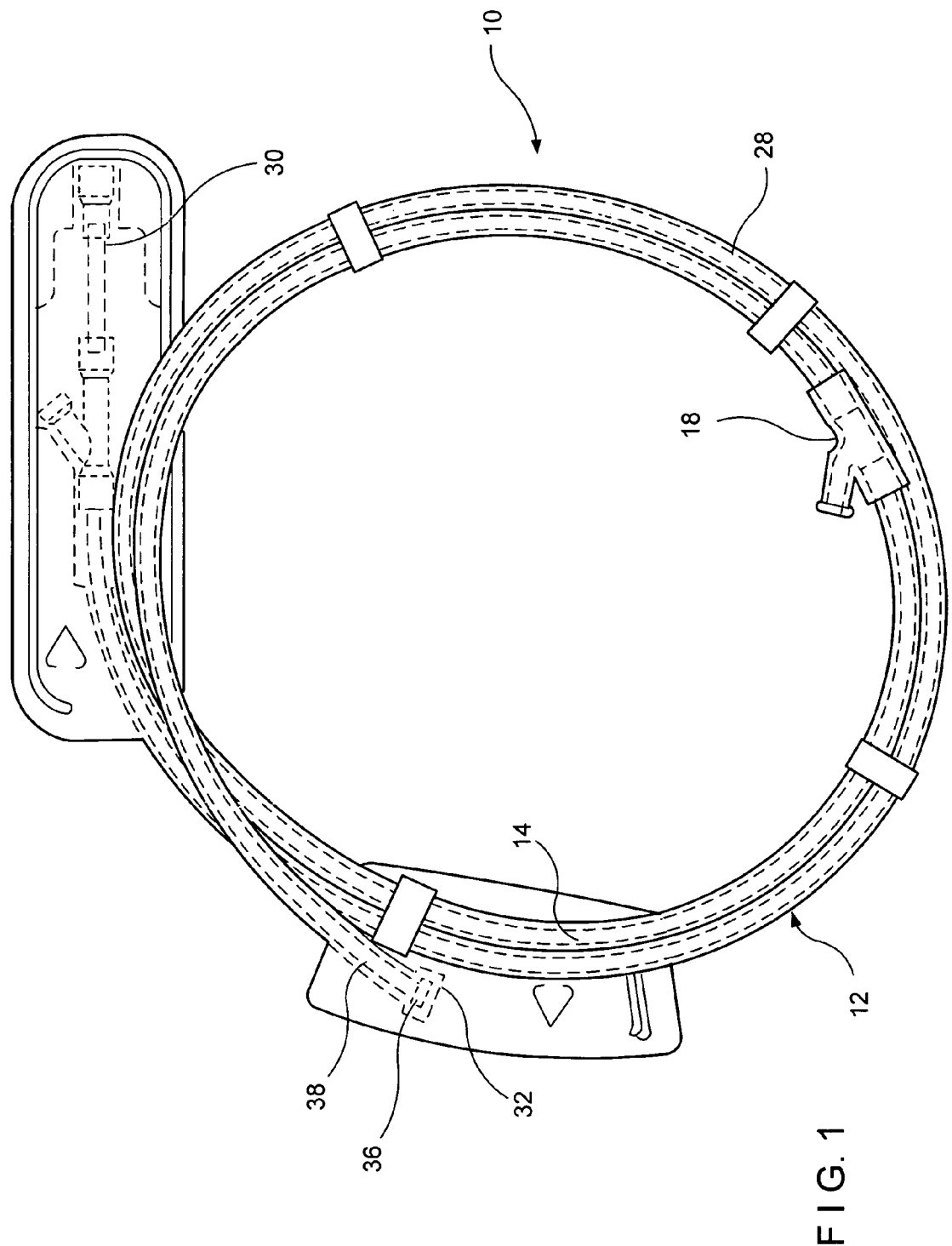
FIG. 1 is a diagram showing a catheter packaging assembly according to an embodiment of the present invention.

The present invention may be further understood with reference to the following description and the appended drawings, wherein like elements are referred to with the same reference numerals. The packaging of catheters presents unique problems, since multiple objectives have to be met by the packaging, while keeping the cost and complexity of the packaging to a minimum. The use of catheters in non-invasive medical procedures has increased rapidly in recent years. Thus, the economic results of improvements in the packaging of these devices can be significant. This is especially true since catheters are often designed to be disposed of after a single use. In addition, packaging that simplifies the operations required to prepare the catheter for use can have a significant market impact by saving the physician's time and effort.

Many catheters have specially shaped portions designed to perform specific tasks during surgery. For example, a catheter may have a curved distal end used to more easily thread along the route to a specific location within the body at which the medical procedure for which the catheter is designed takes place. The distal tips of vascular catheters may be curved to facilitate their guidance into desired branches of the vascular system. These catheters are typically very thin, and may be easily damaged during shipping and storage unless protective packaging is provided. In particular, the shaped distal end may be thinner and more easily damaged than the bulk of the catheter body, and may require additional protective structure to be incorporated in the packaging. In addition, special care must be taken in removing the catheter from the packaging, to prevent damage. Those skilled in the art will understand that, although the present description refers principally to catheters, many other elongated medical devices (e.g., guide wires and medical coils) face similar problems and that the solutions provided herein are equally applicable to packaging for these other devices.

In general, the packaging for catheters according to the present invention includes a tubular enclosure into which the catheter is inserted for protection during shipment and pre-use handling. The tubular enclosure includes a lumen that is dimensioned to receive the catheter. This lumen is preferably slightly longer than the catheter to be received therein and an inner diameter of the lumen is preferably slightly greater than an outer diameter of the catheter. In an exemplary embodiment, the tubular enclosure is coiled to form a hoop. This reduces the length of the package, and simplifies handling, since it is simpler to process a generally round or rectangular package than a wire-like package.

Once the catheter or other elongated medical device has been packaged in the tubular enclosure, it is protected from damage due to crushing loads imposed on the packaging, and from kinks due to excessive bending. However, as described above, removing such devices from the current packaging may be difficult as the outer surface of the catheter is in close proximity to the inner surface of the lumen. Friction between the surfaces often poses a significant obstacle to the catheter's removal. The conventional procedure for unpacking these catheters is to open one end of the package's tubular enclosure and pull the catheter out. Since thin catheters are relatively fragile, forcing such a catheter out of its packaging by pulling against this friction may do damage. In particular, catheters with shaped tips and/or narrow diameters are especially susceptible to damage if they are pulled out against strong frictional forces.

An alternative to pulling the catheter out of its packaging is to cut the packaging open, or otherwise disassemble the tubular enclosure so that the catheter can be removed without the need for strenuous pulling to overcome this friction. This approach, however, requires several additional steps to be taken by the practitioner before using the device. This slows the process, and places the product at a competitive disadvantage because of the extra steps required to use the catheter. In addition, the additional handling steps increase the risk of contamination of the catheter. Catheters are shipped in sterile packaging, and any handling may compromise the sterility of the device. Removing the catheter by cutting open the packaging is thus not an optimal solution to the problem.

In a different procedure, the catheter in the packaging can be hydrated, to simplify removal of the catheter from the tubular enclosure. Many catheters have a coating that, when wet, becomes very slippery so that the catheter may be inserted into a body cavity more easily. Accordingly, when the catheter is hydrated with a fluid (for example water) the coating of the catheter becomes slippery, and lubricates the surfaces of the catheter that are in contact with the inner surface of the packaging. It may then be easier to remove the catheter from the package, without damaging the catheter body or the shaped end thereof. If the coating of the catheter is not sufficient to lubricate the assembly, the package may be hydrated using an external lubricant, to further facilitate removal of the catheter from the tubular enclosure.

This method, however, also adds undesirable time consuming steps to the pre-operative procedure that must be carried out to prepare the catheter for use. For example, one or more baths in a saline solution may be used to hydrate the catheter before the device can be removed from its packaging. These steps are often skipped by operating physicians to save time, thereby increasing the risk that the catheter will be damaged when it is pulled out of the tubular enclosure against the friction generated between the catheter and the packaging.

Another approach used to reduce the friction between catheter and package is to flush the tubular enclosure of the package with a fluid. Conventionally, the flushing is done by introducing the flushing fluid at one or both of the open ends of the package, or through flushing adapters located at those ends. However, in the case of long, thin catheters, it may be difficult to force fluid from one end of the flushable tubular enclosure to the opposite end. In that case, one of the ends of the catheter may not be sufficiently hydrated, and may still "stick" within the package, possibly resulting in damage during removal. Alternatively, multiple flushings may be carried out on both ends of the catheter's package, to fully hydrate the entire length of the device. However, this approach requires additional undesirable steps to prepare the catheter for use, which may be skipped by the physician.

In the case of catheters having shaped tips, the difficulty in removing the catheter from the packaging is accentuated as the shaped tip may be easily damaged if removed from the tubular enclosure without proper lubrication. In addition, flushing the catheter from the end of the tubular enclosure containing the shaped tip may also damage the tip. The relatively high pressure of the fluid necessary to hydrate the entire catheter can damage the shape of the tip. Kinks in the catheter can form if the fluid flow bends the catheter over too small a curvature, or pushes it back into the tubular enclosure. If the catheter is hydrated by introducing fluid from the proximal end, special procedures are called for to ensure complete hydration. If the physician does not properly follow those procedures, insufficient lubrication may result increasing the risk of damage to the catheter.

In addition, the operating physician may want to hydrate the catheter before use even if there is no binding due to friction between the catheter and the tubular enclosure. This may be done so that the lubricating properties of the catheter's surface coating are activated. In this case, a hydrating step according to the present invention is always carried out prior to use of the catheter—not only when excessive friction is encountered during unpacking of the device. Furthermore, the longer the catheter is, the more difficult it is to flush from an end of the catheter.

Embodiments of the present invention resolve these and other problems by providing a system to equally hydrate both ends of the catheter within the tubular enclosure, without using excessively high pressures of the hydrating fluid, and without having to repeat the hydration procedure. According to the invention, a mid-stream flushing adaptor is provided on the tubular enclosure, so that the flushing fluid may be introduced near the middle of the catheter rather than at one of the ends. In this manner the flow is divided between two portions of the tubular enclosure, with a first flow stream extending from the mid-stream adapter to a distal end of the catheter, and a second flow stream extending from the mid-stream adapter to a proximal end of the catheter. The exact location of the mid-stream adapted may be adjusted to achieve a desired balance between the amounts of fluid reaching the two ends of the tubular enclosure. For example, the location may be chosen so that the amount of flow reaching the proximal and distal ends of the catheter are substantially equal.

FIG. 1 shows an exemplary embodiment of a package for an elongated medical device according to the present invention. Package 10 is designed to contain and protect an elongated medical device 14 (e.g., a catheter) during shipping and handling. The elongated medical device 14 may be, for example, a micro-catheter having a shaped tip, or any other type of catheter or elongated medical device having a relatively fragile tip. The elongated medical device 14 is contained within a tubular enclosure 12, which has a lumen of dimensions commensurate with the dimensions of the elongated medical device 14. A first end 30 of the tubular enclosure 12 is adapted to receive a proximal end of the elongated medical device 14. A second end 32 of tubular enclosure 12 is adapted to receive a distal end 38 of the elongated medical device 14, including a shaped distal tip 36. The tubular enclosure 12 may be coiled, as shown in the drawing, to form a hoop segment 28.

Figure 2:
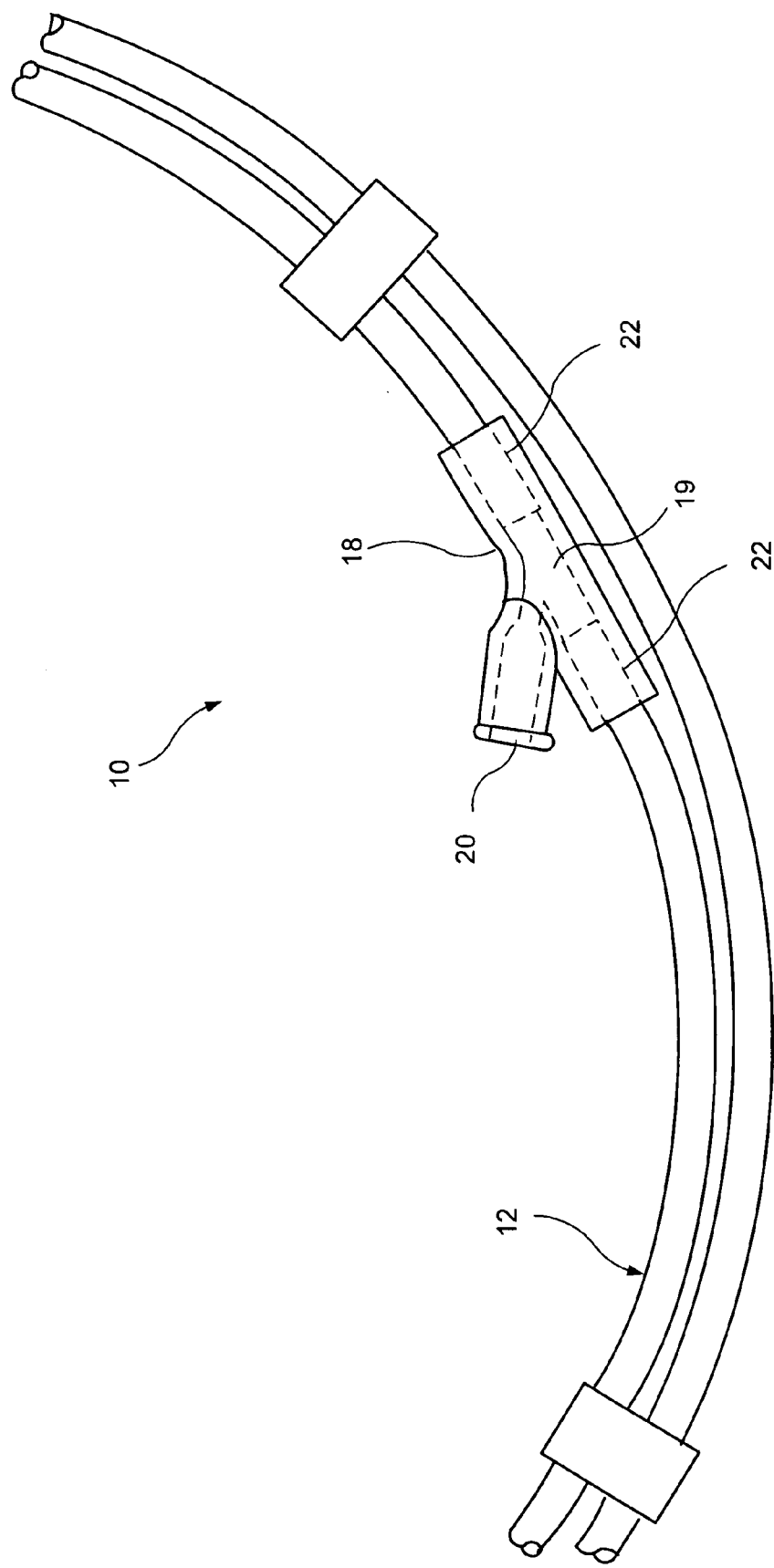
FIG. 2 is a detail view showing a hydrating orifice of the packaging assembly shown in FIG. 1.

As shown more clearly in FIG. 2, the tubular enclosure 12 includes an opening 19 in addition to the opening by which the elongated medical device 14 is inserted into the tubular enclosure 12 that allows access to the internal lumen of the tubular enclosure 12. A flushing adapter 18 may be attached to tubular enclosure 12 at the location of the opening 19, to facilitate introduction of a hydrating fluid into the lumen, and to direct the flow of fluid through the lumen as desired. For example, the flushing adapter 18 may be a rigid thermoplastic luer which may be secured to the tubular enclosure 12 by a UV bond at attachment points 22. The flushing adapter 18 may include an adapter 20 designed to facilitate connection with a source of hydration fluid. For example, adapter 20 may be designed to receive the end of a syringe or an attachment from a pressurized fluid supply as would be understood by those of skill in the art.

In one exemplary embodiment, the flushing adapter 18 may be disposed along the tubular enclosure 12 at a location approximately equidistant from the first end 30 and the second end 32, to achieve a balanced division of flow to the two ends. As indicated above, the exact location of the adapter 18 may be influenced by an amount of flow which is desired to reach each of the ends 30, 32. In a typical exemplary embodiment, the ratio of flow to the two ends is one to one, such that half of the flow reaches each of the catheter's ends 30, 32. However, this ratio may be modified by repositioning the adapter 18 along the tubular enclosure 12. In some cases, the shape of the distal tip 36 may create a resistance to flow at the first end 30 of tubular enclosure 12 that is greater than (or lesser than) the resistance at the second end 32. In that case, the location of flushing adapter 18 may be changed to compensate for the different amounts of blockage so that the desired flow ratio is maintained. In a different embodiment, a different flow balance may be achieved by placing the flushing adapter 18 closer to either one of first and second ends 30, 32, so that a greater proportion of fluid is able to reach the corresponding end.

The shape of the flushing adapter 18 may also be selected to control the way the flow of fluid is divided. As shown in FIG. 2, the adapter 18 is oriented to direct flow preferentially in one direction along the tubular enclosure 12. Thus, a greater percentage of the fluid will reach the corresponding end of elongated medical device 14 than would be the case if this directionality to the flow were not present. The shape of the adapter 18 may be modified to achieve a different balance of the fluid flow, or to divide the flow into equal parts depending on its position along the elongated medical device 14 as would be understood by those of skill in the art. The shape and location of the flushing adapter 18 may thus be selected so that a desired balance of fluid in the various regions of the tubular enclosure 12 is achieved. In some cases this balance will result in the same amount of fluid reaching the proximal and the distal ends of the elongated medical device 14. However, in other cases the desired balance will favor a greater amount of flow reaching one or the other of the two ends.

An additional protective structure 16 may be included in the package 10, to protect the shaped tip 36 of the elongated medical device 14. The protective element 16 may be designed to prevent crushing of the shaped tip 36, and to prevent kinks from developing in case the elongated medical device 14 is bent around too small a radius. Typically this additional protective structure 16 will be used to maintain a desired curvature of the shaped tip 36. In addition, the additional protective structure 16 also provides protection from impact into outside elements such as a pouch or carton.

The flushable tubular enclosure 12 for elongated medical devices 14 according to embodiments of the present invention provides a protective package for the enclosed device, and provides a mechanism for hydrating the device within the tubular enclosure. Hydrating the device according to the present invention does not damage it, because the hydrating fluid is inserted in the tubular enclosure from a position approximately between the two ends of the tubular enclosure. The fluid thus can be at a lower pressure, which does not damage the device therein, and can still reach both distal and proximal ends of the device. A variety of hydration fluids may be inserted according to this method, including water, a saline solution, a disinfecting solution, a lubricant, etc. When necessary, additional structural reinforcements can be added to the packaging to prevent damage to protected portions of the device, such as the shaped distal tip.

The present invention has been described with reference to specific embodiments, more specifically to the packaging used for a micro catheter having a shaped distal tip. However, other embodiments may be devised that are applicable to other medical devices, without departing from the scope of the invention. Accordingly, various modifications and changes may be made to the embodiments without departing from the broadest spirit and scope of the present invention as set forth in the claims that follow. The specification and drawings are accordingly to be regarded in an illustrative rather than restrictive sense.

What is claimed is:

1. A protective package for a catheter, comprising:
a protective sheath including a lumen sized to removably protect a catheter before use, the sheath having a length corresponding to a length of a catheter to be received therein and an inner diameter slightly greater than an outer diameter of a catheter to be received therein, a first end of the sheath being adapted to receive a distal end of a catheter to be received therein and a second end of the sheath being adapted to receive a proximal end of a catheter to be received therein; and
a hydration port located between the first and second ends of the sheath so that a desired proportion of a flushing fluid may be introduced into the lumen near a middle of the sheath and so that a desired proportion of flow thereinto is directed toward the first and second ends of the sheath with a first flow stream extending from the hydration port to the distal end of the catheter and a second flow stream extending from the hydration port to the proximal end of the catheter, wherein the hydration port includes an adapter for connection with a source of the flushing fluid.

2. The protective package according to claim 1, wherein the sheath is formed as a hoop.

3. The protective package according to claim 1, further comprising a protective assembly disposed at the first end of the sheath, the protective assembly being adapted to maintain a desired shape of the distal end of the catheter.

4. The protective package according to claim 3, wherein the protective assembly is adapted to prevent damage to a curvature of the distal end of the catheter.

5. The protective package according to claim 1, wherein the hydration port is adapted to divide a flow of the fluid thereinto to achieve a desired ratio of fluid flow at the first end to fluid flow at the second end.

6. The protective package according to claim 5, wherein the desired ratio is one to one.

7. The protective package according to claim 1, wherein the hydration port is substantially equidistant from the first and second ends.

8. The protective package according to claim 1, wherein the hydration port is oriented to direct an amount of flow toward the first end, and wherein an amount of flow is directed toward the second end.

9. The protective package according to claim 8, wherein the hydration port is positioned so that, the amounts of flow toward the first and second ends achieves a desired ratio of fluid flow at the first end to fluid flow at the second end.

10. The protective package according to claim 9, wherein the desired ratio is one to one.

11. A protective package for a catheter, comprising:
a protective sheath including a lumen sized to removably protect a catheter before use, the sheath having a length corresponding to a length of a catheter to be received therein and an inner diameter slightly greater than an outer diameter of a catheter to be received therein, a first end of the sheath being adapted to receive a distal end of a catheter to be received therein and a second end of the sheath being adapted to receive a proximal end of a catheter to be received therein;
a hydration opening into the lumen between the first and second ends of the sheath so that a desired proportion of a flushing fluid may be introduced into the lumen near a middle of the sheath and so that a desired proportion of flow thereinto is directed toward the first and second ends of the sheath with a first flow stream extending from the hydration opening to the distal end of the catheter and a second flow stream extending from the hydration opening to the proximal end of the catheter; and
a luer attached to the sheath in fluid contact with the lumen, the luer defining the hydration opening.

12. A catheter kit comprising:
a catheter having a distal end and a proximal end; and
a catheter packaging comprising:
a tubular enclosure removably protecting the catheter before use, the tubular enclosure having a length corresponding to a length of the catheter and an inner diameter defining a lumen that is slightly greater than an outer diameter of the catheter, a first end of the tubular enclosure being adapted to receive the distal end and a second end of the tubular enclosure being adapted to receive the proximal end of the catheter; and
a hydration port extending into the lumen between the first and second ends of the tubular enclosure, the hydration port being positioned so that a desired proportion of flow of a flushing fluid that may be introduced into the lumen enters the lumen near a middle of the enclosure and is directed toward the first and second ends of the enclosure such that a first flow stream extends from the hydration port to the distal end of the catheter and a second flow stream extends from the hydration port to the proximal end of the catheter, wherein the hydration port includes an adapter for connection with a source of the flushing fluid.

13. The catheter kit according to claim 12, further comprising a protective structure disposed at the first end, the protective structure maintaining a desired curvature of a shaped distal tip of the catheter.

14. The catheter kit according to claim 12, wherein the tubular enclosure is coiled to form a hoop.

15. The catheter kit according to claim 12, wherein a hydrating fluid introduced into the tubular enclosure via the hydration port is divided such that the proximal end and the distal end of the catheter are substantially equally hydrated.

16. The catheter kit according to claim 12, wherein the catheter is a micro-catheter with a shaped distal tip.

17. The catheter kit according to claim 12, wherein the hydration port is substantially equidistant between the first and second ends.

18. A protective package for removably receiving an elongated medical device, comprising:
a protective sheath including a lumen sized to tightly fit the elongated medical device to be removably received therein to protect the elongated device before use, the sheath having a length corresponding to a length of the medical device and an inner diameter slightly greater than an outer diameter of the elongated device, a first end of the sheath being adapted to receive a distal end of the elongated medical device and a second end of the sheath being adapted to receive a proximal end of the elongated medical device; and
a hydration port located near a middle of the sheath so that a desired proportion of a flushing fluid that may be supplied to the sheath via the hydration port is directed toward the first and second ends of the sheath with a first flow stream extending from the hydration port to the distal end of the elongated device and a second flow stream extending from the hydration port to the proximal end of the elongated device, wherein the hydration port includes an adapter for connection with a source of the flushing fluid.

19. The protective package according to claim 18, wherein a portion of the lumen for receiving a distal end of the elongated medical device is curved in a manner complimenting a preformed curve of the distal end of the medical device.

20. The protective package according to claim 18, wherein a first portion of the lumen for receiving a distal end of the elongated medical device has a first diameter different than a second diameter of a second portion of the lumen for receiving a proximal end of the elongated medical device, the differences in the diameters of the first and second portions corresponding to differences in diameter between the proximal and distal portions of the elongated medical device.

21. The protective package according to claim 18, wherein the first diameter is less than the second diameter.

22. The protective package according to claim 18, further comprising a reinforced end of a first portion of the lumen for receiving a distal end of the elongated medical device to protect the distal end of the elongated medical device.

23. A protective package for removably receiving an elongated medical device, comprising:
a protective sheath including a lumen sized to tightly fit a body of the elongated medical device to be received therein, the sheath removably protecting the elongated medical device before use, a first end of the sheath being adapted to receive a distal end of the elongated medical device and a second end of the sheath being adapted to receive a proximal end of the elongated medical device, a length of the sheath corresponding to a length of the elongated medical device and an inner diameter of the lumen being slightly greater than an outer diameter of the elongated medical device; and
a hydration port located between the first and second ends of the sheath, the hydration port being positioned so that a flushing fluid that may be supplied to the hydration port is supplied to the lumen near a middle of the sheath with a desired proportion of flow thereinto being directed toward the first and second ends of the sheath such that a first flow stream extends from the hydration port to the distal end of the elongated medical device and a second flow stream extends from the hydration port to the proximal end of the elongated medical device, wherein the hydration port includes an adapter for connection with a source of the flushing fluid.

24. A packaging method for a catheter comprising:
providing a catheter having a distal end and a proximal end;
providing a shipping packaging in the form of a tubular enclosure having a length corresponding to a length of the catheter and an inner diameter defining a lumen that is slightly greater than an outer diameter of the catheter, a first end of the tubular enclosure being adapted to receive the distal end; a second end of the tubular enclosure being adapted to receive the proximal end of the catheter;

providing the tubular enclosure with a hydration port between the first and second ends of the tubular enclosure, the hydration port being positioned so that a desired proportion of a flow of flushing fluid that may be introduced into the lumen via the hydration port enters the lumen near the middle of the catheter is directed toward the first and second ends of the enclosure such that a first flow stream extends from the hydration port to the distal end of the catheter and a second flow stream extends from the hydration port to the proximal end of the catheter, wherein the hydration port includes an adapter for connection with a source of the flushing fluid; and removably inserting the catheter into the lumen of the tubular enclosure.

25. A catheter packaging comprising:

a tubular enclosure having a first end and a second end for removably protecting a catheter having a shaped distal tip and a proximal end, the tubular enclosure having a length corresponding to a length of the catheter and an inner diameter defining a lumen that is slightly greater than an outer diameter of the catheter; a first end of the tubular enclosure being adapted to receive the shaped distal tip distal end; a second end of the tubular enclosure being adapted to receive the proximal end of the catheter;

a hydration port located between the first and second ends of the tubular enclosure, the hydration port being positioned so that a desired proportion of a flow of a flushing fluid that may be introduced into the lumen via the hydration port enters the lumen near the middle of the tubular enclosure and is directed toward the first and second ends of the enclosure such that a first flow stream extends from the hydration port to the distal end of the catheter and a second flow stream extends from the hydration port to the proximal end of the catheter, wherein the hydration port includes an adapter for connection with a source of the flushing fluid; and an additional protective structure disposed at the first end of the tubular enclosure adapted to prevent crushing of the shaped distal tip.

* * * * *